(12) United States Patent
Adelson et al.

(10) Patent No.: US 9,538,056 B2
(45) Date of Patent: *Jan. 3, 2017

(54) HIGH-RESOLUTION SURFACE MEASUREMENT SYSTEMS AND METHODS

(71) Applicant: MASSACHUSETTS INSTITUTE OF TECHNOLOGY, Cambridge, MA (US)

(72) Inventors: Edward H. Adelson, Winchester, MA (US); Micah K. Johnson, West Roxbury, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/677,394

(22) Filed: Apr. 2, 2015

(65) Prior Publication Data
US 2016/0044218 A1    Feb. 11, 2016

Related U.S. Application Data

(63) Continuation of application No. 13/561,712, filed on Jul. 30, 2012, now Pat. No. 9,127,938.

(60) Provisional application No. 61/512,680, filed on Jul. 28, 2011.

(51) Int. Cl.
| | | |
|---|---|---|
| H04N 9/47 | (2006.01) | |
| H04N 7/18 | (2006.01) | |
| H04N 5/225 | (2006.01) | |
| A61B 5/00 | (2006.01) | |
| A61B 5/117 | (2016.01) | |
| G01B 11/30 | (2006.01) | |
| G06F 3/03 | (2006.01) | |

(52) U.S. Cl.
CPC ........... *H04N 5/2256* (2013.01); *A61B 5/0077* (2013.01); *A61B 5/1172* (2013.01); *A61B 5/441* (2013.01); *G01B 11/30* (2013.01); *G01B 11/303* (2013.01); *G06F 3/0304* (2013.01)

(58) Field of Classification Search
USPC ........... 348/77, 78, 79, 68, 92, 49, 128, 131, 348/217.1, 227.7, 234, 236, 237, 238, 348/258, 267, 349, 366, 370, 474, 602, 348/636, 680, 719, 801, 813; 362/235, 362/296.01, 351, 540; 359/883
See application file for complete search history.

(56) References Cited

U.S. PATENT DOCUMENTS

| | | | | |
|---|---|---|---|---|
| 6,518,034 B1 * | 2/2003 | Phillips | .................... | C12Q 1/54 435/14 |
| 6,897,832 B2 * | 5/2005 | Essig, Jr. | ................ | E04H 15/20 342/10 |
| 7,577,469 B1 * | 8/2009 | Aronowitz | ......... | A61B 5/14532 600/310 |
| 2002/0036801 A1 * | 3/2002 | Ho | ........................... | G06T 9/00 358/1.16 |

(Continued)

*Primary Examiner* — Jefferey Harold
*Assistant Examiner* — Mustafizur Rahman
(74) *Attorney, Agent, or Firm* — Gesmer Updegrove LLP

(57) ABSTRACT

This disclosure provides systems, devices, and methods for capturing and measuring surface topography. This disclosure provides a high resolution retrographic sensor comprising a volume of elastomer and a thin, opaque reflective membrane. The reflective membrane is arranged to conform to a specimen that contacts it. The disclosure provides a high resolution visualization system comprising the retrographic sensor and an illumination source. Also provided are high resolution measurement systems comprising the retrographic sensor, an illumination source, an imaging device, and a processing component.

24 Claims, 17 Drawing Sheets

(56) References Cited

U.S. PATENT DOCUMENTS

| | | | | |
|---|---|---|---|---|
| 2003/0129451 A1* | 7/2003 | Nukada | ............... | H01L 51/0035 |
| | | | | 428/690 |
| 2005/0048376 A1* | 3/2005 | Eschbach | ................... | G03F 1/64 |
| | | | | 430/5 |
| 2006/0098237 A1* | 5/2006 | Steinberg | ........... | H04N 5/23212 |
| | | | | 358/302 |
| 2007/0098393 A1* | 5/2007 | Hagiwara | ................ | G03B 7/08 |
| | | | | 396/241 |
| 2007/0154561 A1* | 7/2007 | Takeda | .................... | A61K 8/19 |
| | | | | 424/489 |
| 2008/0128287 A1* | 6/2008 | Wu | ........................ | B82Y 20/00 |
| | | | | 205/109 |
| 2009/0147110 A1* | 6/2009 | Muramatsu | .......... | H04N 5/3572 |
| | | | | 348/255 |
| 2010/0294350 A1* | 11/2010 | Ko | ....................... | H01G 9/2031 |
| | | | | 136/255 |

* cited by examiner

FIG. 9A
FIG. 9B
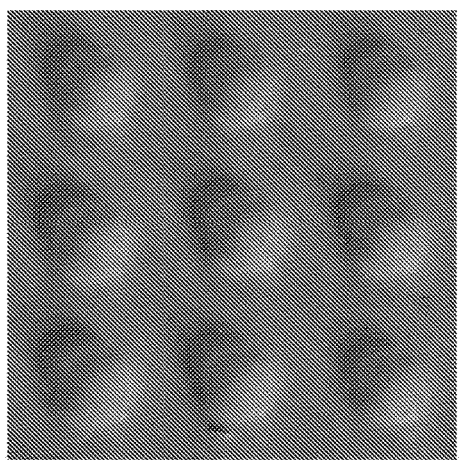
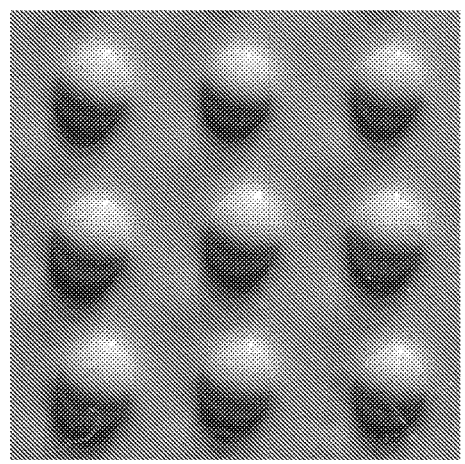
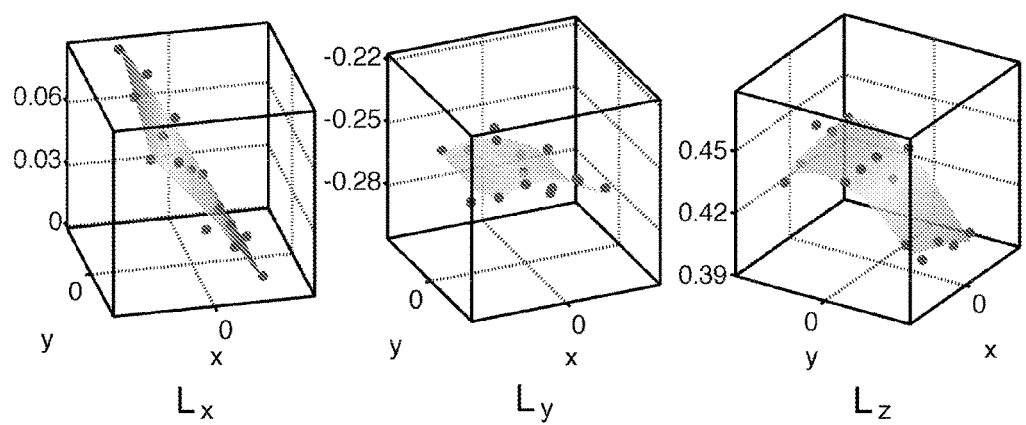
FIG. 9C

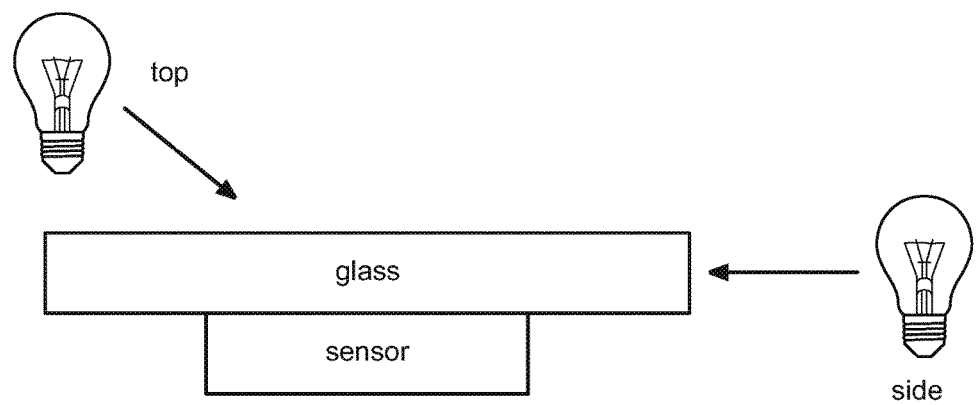
FIG. 14D
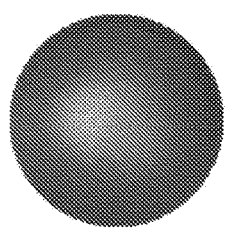 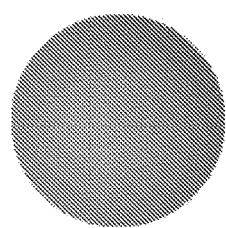 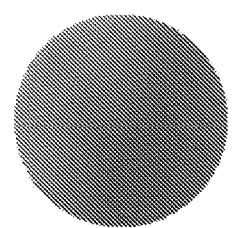
Bronze flakes
top illumination
Silver powder
top illumination
Silver powder
side illumination
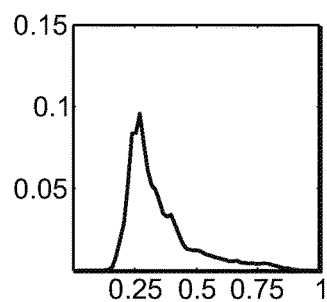 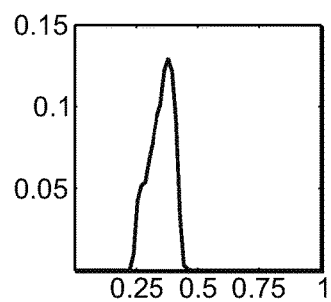 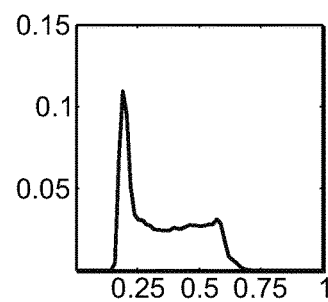
FIG. 14A  FIG. 14B  FIG. 14C

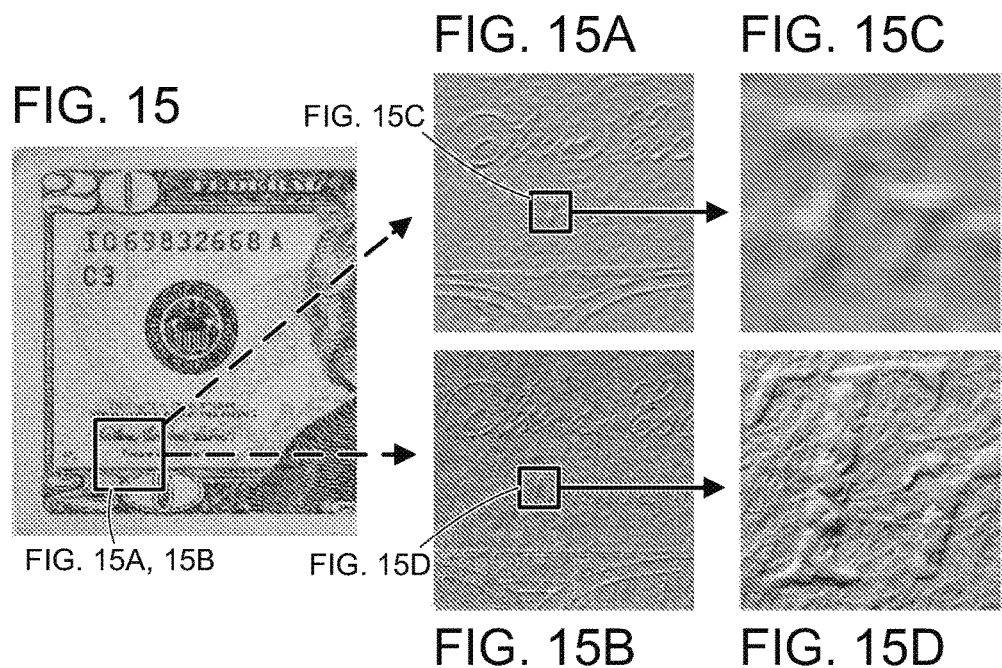
FIG. 15  FIG. 15A  FIG. 15B  FIG. 15C  FIG. 15D
(a) lookup table  
FIG. 16A
(b) our method  
FIG. 16B (b) portable configuration (a) bench configuration

HIGH-RESOLUTION SURFACE MEASUREMENT SYSTEMS AND METHODS

PRIORITY

This application is a continuation of U.S. application Ser. No. 13/561,712 filed Jul. 30, 2012, which claims priority to U.S. Provisional Application No. 61/512,680, filed Jul. 28, 2011. The entire contents of that these applications are incorporated herein by reference.

STATEMENT OF GOVERNMENT RIGHTS

Sponsorship Information

This invention was made with Government support under Grant No. DMS0739255 awarded by the National Science Foundation and under Grant No. R01 EY019262 awarded by the National Institutes of Health. The Government has certain right in the invention.

FIELD OF INVENTION

This disclosure relates to the field of profilometry and high-resolution surface imaging and measurement.

BACKGROUND OF INVENTION

In industrial inspection, it is often important to measure the roughness of a manufactured surface, or the presence of defects such as cracks, pits, or gouges. There are instruments commercially available for surface metrology, including diamond scribe profilometers and non-contact optical profilometers. However, these devices have various limitations in terms of their expense, their portability, their accuracy, and the speed at which they provide measurements.

There are also various methods for getting 3D surface data by optical means, including structured light, depth from defocus, photometric stereo, and multiview stereopsis. However, these techniques work best on materials that are matte and opaque. Specular, translucent, or transparent materials are more difficult for these techniques, and many of the materials of greatest interest are in these categories.

One domain of particular importance for detailed topography is skin profilometry. Skin has both translucency and specularity, making its topography difficult to measure by standard optical means. Dermatologists, cosmetic surgeons, cosmetic manufacturers, and cosmetic consumers, are often interested in measuring the topography of the skin. For example, topography is measured before and after a wrinkle reduction treatment to quantify the treatment's efficacy. Due to the optical challenges, a popular method of measuring skin topography is to make a silicone replica of the skin and then to perform profilometry on the replica. This is slow and inconvenient. There are also specialized optical skin profilometers designed to overcome the optical challenges posed by human skin, from such companies as GFMesstechnik of Germany (e.g., the PRIMOS), and Courage-Khazaka of Germany (e.g., the Visiometer). These devices tend to be expensive and slow due to the hardware and software that are required to overcome the fact that skin is neither matte nor opaque.

Thus, there is a need to examine and measure the detailed topography of various surfaces inexpensively, quickly, and accurately.

SUMMARY OF THE INVENTION

One aspect of this disclosure is directed to a high-resolution retrographic sensor for measuring or visualizing the surface of a specimen brought into contact with the sensor. The retrographic sensor comprises a volume of elastomer covered with a reflective membrane. The elastomer is capable of transmitting an image. The reflective membrane is thin, opaque, and capable of reflecting light.

In some embodiments, the elastomer has a hardness between 10 and 100 on the Shore A scale. In some embodiments, the elastomer has a hardness between 10 and 100 on the Shore 00 scale. In some embodiments, the elastomer is softer than 10 on the Shore 00 scale. In some embodiments, the elastomer is softer than the specimen contacting it. In some embodiments, the elastomer is tacky.

In some embodiments, the reflective membrane is elastomeric. In some embodiments, the reflective membrane is harder than the elastomer which it covers. In other embodiments, the reflective membrane has about the same hardness as the elastomer which it covers. In some embodiments, the reflective membrane is arranged to conform to a specimen that contacts the reflective membrane.

The reflective membrane is thin. In some embodiments, the reflective membrane is equal to or less than about 10 microns thick. In other embodiments, the reflective membrane is less than about 5 microns thick. In other embodiments, the reflective membrane is less than about 1 micron thick.

In some embodiments, the reflective membrane has an opacity of 50% or less. In some embodiments, the reflective membrane has an opacity of at least 50%. In some embodiments, the reflective membrane has an opacity of at least 75%. In some embodiments, the reflective membrane has an opacity of at least 90%. In some embodiments, the reflective membrane has an opacity of at least about 99%. In some embodiments, the reflective membrane is 100% opaque.

In some embodiments, the reflective membrane is matte. In other embodiments, the reflective membrane is specular. In some embodiments, the membrane's reflectivity lies somewhere between matte and specular. In some embodiments, the reflective membrane has a non-granular appearance.

In some embodiments, the reflective membrane has low reflectance in at least one color channel. In some embodiments, the reflective membrane has a reflectance between about 1% and about 50%. In some embodiments, the reflective membrane is gray. In other embodiments, the reflective membrane is a color other than gray.

In some embodiments, the reflective membrane comprises reflective particles with a mean diameter of less than about 2 microns. In some embodiments, the reflective membrane comprises reflective particles with a mean diameter of less than 1 micron. In some embodiments, the reflective particles are metal. In some embodiments, the reflective particles are isotropic in morphology. In some embodiments, the reflective membrane comprises a monolayer of reflective particles.

Another aspect of this disclosure is directed to a high-resolution visualization system. The high-resolution visualization system includes the retrographic sensor of this disclosure supported on a clear rigid support. The high-resolution visualization system also includes a source of, or path for, illumination that is positioned to illuminate the reflective membrane. In some embodiments, the high-resolution visualization system also includes, an imaging device positioned to receive light reflected from the reflective membrane in the form of an image.

In some embodiments, the rigid support comprises glass. In other embodiments, the rigid support comprises a clear polymer.

In some embodiments, the source of illumination includes one light source. In other embodiments, the source of illumination includes more than one light source. In some embodiments, the source of illumination illuminates the reflective membrane at a grazing angle. In other embodiments, the high-resolution visualization system includes a light path configured to allow ambient light or an external light source to illuminate the reflective membrane. In some embodiments, the light path is configured to allow an external light source to illuminate the reflective membrane at a grazing angle.

In some embodiments, the imaging device includes a camera. In some embodiments, the imaging device includes an array of sensing elements.

In some embodiments, the high-resolution visualization system is configured to visualize human skin. In some embodiments configured to visualize human skin, the elastomer is soft and tacky and the reflective membrane is approximately as soft as the elastomer.

In some embodiments, the high-resolution visualization system is configured as a benchtop system. In some embodiments, the high-resolution visualization system is portable. In some embodiments where the high-resolution visualization system is portable, it is hand-held.

Another aspect of this disclosure is directed to a high-resolution measurement system. The high-resolution measurement system includes the retrographic sensor of this disclosure supported on a clear rigid support, a source of, or path for, illumination positioned to illuminate the reflective membrane, an imaging device positioned to receive light reflected from the reflective membrane in the form of an image, and a processing component coupled to the imaging device and configured to calculate and output measurement information based on image information received from the imaging device.

In some embodiments, the source of illumination includes one light source. In other embodiments, the source of illumination includes more than one light source. In some embodiments, the source of illumination illuminates the reflective membrane at a grazing angle. In other embodiments, the high-resolution visualization system includes a light path configured to allow ambient light or an external light source to illuminate the reflective membrane. In some embodiments, the light path is configured to allow an external light source to illuminate the reflective membrane at a grazing angle.

In some embodiments, the imaging device includes a camera. In some embodiments, the imaging device includes an array of sensing elements. In some embodiments, the imaging device is configured to output image information.

In some embodiments, the processing component is configured to calculate measurement information using shape from shading techniques, including, but not limited to, shape from shading. In some embodiments, the processing component is configured to calculate measurement information using photometric stereo techniques. In some embodiments, the processing component is configured to calculate measurement information using algorithms described herein.

In some embodiments, the high-resolution measurement system is configured to measure human skin. In some embodiments configured to measure human skin, the elastomer is soft and tacky and the reflective membrane is approximately as soft as the elastomer.

In some embodiments, the high-resolution measurement system is configured as a benchtop system. In some embodiments, the high-resolution measurement system is portable. In some embodiments where the high-resolution measurement system is portable, it is hand-held.

In another aspect, the disclosure is directed to methods of visualizing surface topography at high-resolution. In this method, the retrographic sensor is provided on a clear rigid support. Then, the reflective membrane of the retrographic sensor of this disclosure is contacted with a specimen. Next, the reflective membrane of the retrographic sensor is illuminated with one or more light sources. Light is reflected from the reflective membrane in the form of an image. Visualization is accomplished when a person views the image directly or through magnifying or other optics, or an imaging device receives an image which indicates one or more features of the specimen.

In some embodiments, the light reflected from the reflective membrane may be viewed directly with a human eye or through magnifying optics. Alternatively, in other embodiments, an imaging device is positioned to receive light reflected from the reflective membrane in the form of an image.

In some embodiments, the imaging device includes a camera. In some embodiments, the imaging device includes an array of sensing elements.

In some embodiments, the reflective membrane is illuminated with one light source. In other embodiments, the reflective membrane is illuminated with more than one light source. In some embodiments, the reflective membrane is illuminated with more than one light source from multiple directions. In some embodiments, the reflective membrane is illuminated at a grazing angle by one or more light sources. In some embodiments, three dimensional topography is visualized.

In some embodiments, the method also comprises eliminating small air bubbles that may be trapped between the reflective membrane and the specimen. In some such embodiments, the reflective membrane's surface is made with a microtexture that allows air egress when the membrane is pressed against the specimen. In some such embodiments, the reflective membrane is covered with a fine powder that allows air egress when the membrane is pressed against the specimen.

In some embodiments, the specimen, or the membrane, or both, are wetted with a liquid that displaces air, and the membrane and specimen are pressed together. In some such embodiments, the visualization occurs after the membrane and specimen have been pressed together for a period of time sufficient to allow at least a portion of the liquid to be absorbed by the specimen, the sensor, of both, thereby allowing the membrane to conform to the specimen with little or no air.

In some embodiments, a fine powder comprising air passages is applied to the reflective membrane, or the specimen, or both, before the reflective membrane is contacted with a specimen. In some embodiments, the fine powder is talc, silica, calcium carbonate, or zinc stearate.

In another aspect, the disclosure is directed to methods of measuring surface topography at high-resolution. In this method, the retrographic sensor is provided on a clear rigid support. Then, the reflective membrane of the retrographic sensor is contacted with a specimen. Next, the reflective membrane of the retrographic sensor is illuminated with one or more light sources. Next, an imaging device is positioned to receive light reflected from the reflective membrane in the form of an image. The imaging device is configured to output image information. Then, a processing component is coupled to the imaging device, wherein the processing component is configured to calculate and output measurement information based on image information received from the imaging device.

In some embodiments, the reflective membrane is illuminated with one light source. In other embodiments, the reflective membrane is illuminated with more than one light source. In some embodiments, the reflective membrane is illuminated with more than one light source from multiple directions. In some embodiments, the reflective membrane is illuminated at a grazing angle by one or more light sources. In some embodiments, the methods measure three dimensional topography.

In some embodiments, the imaging device includes a camera. In some embodiments, the imaging device includes an array of sensing elements.

In some embodiments, the processing component calculates measurement information using shape from shading techniques. In some embodiments, the processing component calculates measurement information using photometric stereo techniques. In some embodiments, the processing component calculates measurement information using algorithms described herein.

In some embodiments, the method also comprises eliminating small air bubbles that may be trapped between the reflective membrane and the specimen. In some such embodiments, the reflective membrane's surface is made with a microtexture that allows air egress when the membrane is pressed against the specimen. In some such embodiments, the reflective membrane is covered with a fine powder that allows air egress when the membrane is pressed against the specimen.

In some embodiments, the specimen, or the membrane, or both, are wetted with a liquid that displaces air, and the membrane and specimen are pressed together. In some such embodiments, the visualization occurs after the membrane and specimen have been pressed together for a period of time sufficient to allow at least a portion of the liquid to be absorbed by the specimen, the sensor, of both, thereby allowing the membrane to conform to the specimen with little or no air.

In some embodiments, a fine powder comprising air passages is applied to the reflective membrane, or the specimen, or both, before the reflective membrane is contacted with a specimen. In some embodiments, the fine powder is talc, silica, calcium carbonate, or zinc stearate.

Another aspect of this disclosure is directed to methods of manufacturing the retrographic sensor of this disclosure. A volume of elastomer is provided. In some embodiments, the elastomer is coated with a thin, opaque, reflective membrane. In some embodiments, the elastomer is tacky. In some embodiments, reflective particles are applied to at least one surface of the elastomer. In some embodiments, the reflective particles are dusted on to at least on surface of the elastomer. In some embodiments, the reflective particles comprise non-specular metal powder.

In some embodiments, the coating step includes brushing, daubing, dipping, or spraying. In some embodiments, the coating step includes applying an elastomeric ink comprising pigment particles and an elastomeric binder. In some embodiments, the coating step comprises applying pigment particles directly to the surface of the volume of elastomer. In such embodiments, the application of particles can be by brushing, or dusting.

BRIEF DESCRIPTION OF THE DRAWINGS

FIG. 9A shows an image of a calibration target for a computer model of spatially-varying illumination using multiple light directions. FIG. 9B shows a single channel of the calibration target image of FIG. 9A. FIG. 9C shows spatial variation of the coefficients modeled with a quadratic surface.

FIGS. 14A-14D show an illumination design for different pigments.

FIGS. 15A-15E show comparisons of the high-resolution measurement using the previous retrographic system and the system of this disclosure.

FIGS. 16A-16B show the effect of shadows in photometric stereo.

DETAILED DESCRIPTION OF THE INVENTION

Figure 1:
FIG. 1 shows an embodiment of the handheld portable surface measurement system connected to a laptop computer.

This disclosure provides sensors, systems, and methods that allow for efficient, accurate visualization and measurement of shallow relief geometry, regardless of the light scattering behavior of the material. Aspects of the sensor construction, lighting design, and reconstruction algorithm allow the retrographic sensor to be capable of high-resolution and to be constructed in a portable form.

The retrographic sensor of this disclosure has two components: a volume of elastomer and a reflective membrane. When a specimen is brought into contact with the reflective membrane of the retrographic sensor, the reflective membrane conforms to the surface of the specimen. For each component, there are a variety of options that influence the ability to visualize and measure surface topography at high-resolution. The retrographic sensor can be designed in accordance with the properties and surface features of a specimen to be contacted with the sensor.

The Elastomer

The retrographic sensor comprises a clear elastomer capable of transmitting an image. The elastomer can be comprised of a wide range of materials including, but not limited to, silicone rubber, polyurethane, thermoplastic elastomer, plastisol, natural rubber, polyisoprene, polyvinyl chloride, gelatin, hydrogel, or a mixture thereof. The clear elastomer can be composed of a sticky or tacky material. Examples of sticky or tacky elastomers include, but are not limited to, 3M's VHB tape, soft thermoplastic elastomers such as HSSG-20 from Crinnis Consulting, soft silicones such as Dow Corning Sylgard 527, and the like. The hardness of the elastomer ranges between about 5 on the Shore 000 scale to about 100 on the Shore A scale. The hardness of the elastomer can be selected depending on the high-resolution application for which the sensor is being designed.

The Reflective Membrane

The reflective membrane is also elastomeric, and typically has a hardness that is equal to or greater than that of the clear elastomer body. The reflective membrane may be comprised of the same material as the elastomer, or of a different material. In general, the reflective membrane is thin, opaque, and capable of reflecting light.

The reflective membrane comprises reflective particles in a layer that is thick enough to be opaque, but thin enough to allow it to conform to fine surface structure. The resolution of the system, i.e., the ability of the system to visualize or measure small surface details, is approximately proportional to the thickness of the reflective membrane. In some embodiments, the layer of particles is a monolayer. In some embodiments, the reflective membrane is equal to or less than about 10 microns thick. In other embodiments, the reflective membrane is equal to or less than about 5 microns thick. In other embodiments, the reflective membrane is equal to or less than about 1 micron thick. If surface features below a given size are unnecessary for the application, the reflective membrane can be thicker. Thicker membranes tend to be more robust since there can be multiple layers of reflective pigments and a protective coating.

One goal of the reflective membrane is to reduce or remove the influence of the optical properties of the specimen on the resulting image. In this way, the resulting image is primarily the result of the specimen's surface topography, coupled with the membrane's reflectivity and the illumination. The image is largely independent of the original optical properties of the specimen, such as specularity, transparency, or variegated albedo, since all or most of the light is reflected by the opaque membrane, rather than the specimen itself. In one embodiment, the reflective membrane is 100% opaque, i.e., opaque to all visible wavelengths so that no light rays reach the underlying surface. In other embodiments, the reflective membrane has an opacity of 99% or better. In other embodiments, the reflective membrane has an opacity of more than 50%. In some embodiments, the reflective membrane can be designed to be reflective for some wavelengths (e.g., visible) and transmissive for other wavelengths. In some embodiments, the reflective membrane comprises non-transmitting particles.

Semi-specular reflective membranes comprised of fine metal flakes were described in U.S. patent application Ser. No. 12/488,088, the disclosure of which is incorporated herein by reference. That type of reflective membrane on a clear elastomer allows for high optical gain, in that small variations in surface normal lead to large changes in reflected luminance, allowing one to detect subtle variations in surface normal. However, for a single illumination direction, specular or semi-specular surfaces can be dark for many surface orientations. The mathematical models for specular and semi-specular surfaces can also be complex. For these reasons, in some embodiments the sensors and systems of this disclosure use matte reflective membranes for high-resolution visualization and measurement.

In some embodiments, the reflective membrane comprises metal flakes. The metal flakes used in membranes as described in U.S. patent application Ser. No. 12/488,088 were large (2 microns or more). The shape and size of the flakes cause the reflective membrane to have a random granular appearance at a fine scale, which acts as a source of noise and makes it difficult to resolve very fine details. In some embodiments for high resolution, the reflective membrane comprises reflective particles that have a mean diameter of less than about 2 microns. In some embodiments, the reflective membrane comprises reflective particles that have a mean diameter of less than about 1 micron.

For high-resolution visualization and measurements, the reflective membrane may comprise fine particles. The use of very fine particles results in the reflective membrane appearing "grainless" or "non-granular." The shape of the particles also influences the grainless appearance of the membrane. Metal flakes act like microscopic mirrors and create strong reflections in certain directions. Spherical particles have a larger distribution of angles, which affects the distribution of light rays. In some embodiments, these fine particles are below the resolution of the optical system so that the image captured by the system appears grainless. For example, submicron silver particles with near-spherical morphology, such as product 47MR-21S from Inframat Advanced Materials, are appropriate when the optical system is designed to resolve features larger than 1 micron. Other metal powders with submicron particle size can also be used.

The reflective membrane can stretch to conform to the surface of a structure that contacts it. In one embodiment, the reflective membrane is made from the same material as the underlying elastomer and, therefore, has the same elastic properties. In some embodiments, the reflective membrane is softer than the underlying elastomer. In other embodiments, the reflective membrane is stiffer than the underlying elastomer. When the reflective membrane is stiffer than the underlying elastomer, it can pucker or wrinkle when the retrographic sensor is in use.

The reflective membrane comprises particles capable of reflecting light. The particles can be chosen such that the resulting membrane has reflective properties that range from shiny to diffuse, dark to bright, and opaque to transmissive for specified wavelengths of light. In some embodiments, the reflective membrane comprises metal particles. For high-resolution visualization and measurement, there can be advantages to using a diffuse membrane that is dark gray, or more generally, has low reflectance for some wavelengths. If the membrane is white, then light reflecting off of one point on the surface will illuminate other points on the surface. The resulting illumination at any point on the surface will be the combination of direct illumination, i.e., directly from the light source, and indirect illumination consisting of reflected light from other points on the surface. Indirect illumination, often called interreflections, is more complicated for any 3D photometric stereo algorithm since it is dependent on the surface structure, which is being estimated by the algorithm. When the membrane is dark gray, i.e., less than 50% reflectance, the amount of interreflection between particles is reduced. The membrane cannot have 0% reflectance since some rays must reflect back to the imaging system in order to be imaged. Accordingly, in one embodiment, the reflective membrane has less than 50% reflectance. In other embodiments, the reflective membrane has less than 25% reflectance. In other embodiments, the reflective membrane has less than 10% reflectance. In some embodiments, the reflective membrane has a reflectance between about 1% and about 50%. In some embodiments, the reflective membrane is gray.

The reflectance of the reflective membrane can be designed to be low with respect to specific wavelengths. If the membrane is colored (e.g., red) it will have high reflectance for illumination that tends towards red (long wavelengths) and low reflectance for illumination that tends towards green or blue (shorter wavelengths). Accordingly, in some embodiments, the reflective membrane is a color other than gray.

The reflective membrane can comprise combinations of traditional paint pigments. For example, titanium dioxide and carbon black can be mixed to form a gray colored paint. In addition, there are single pigments made of metal compounds, including metal oxides and sulfides, which, when in a very fine powder, yield a paint that is gray or some other dark color. Fine metal powders offer a particularly good combination of opacity and uniformity, while also producing a membrane that is gray in color. Silver, nickel, and aluminum are examples of metals that form suitable fine powders.

Systems for High-Resolution Image Capture and Measurement

The systems in this disclosure allow for the capture of microgeometry that has previously been difficult to measure, such as the narrow grooves of brushed metal, the spacing of threads in fine fabric, or minute and intricate folds of skin. Such microgeometry has value across numerous industries, including aerospace, consumer goods, entertainment, and science. Virtually, any industry that manufactures or studies surfaces can benefit from fast and accurate methods for visualization and measurement. In addition, the portable configuration provides particular benefits by allowing for capture of surface geometry in seconds, in-place, and without harming the subject.

The retrographic sensor allows a specimen to be covered with a reflective membrane that can be designed with material of a known reflectance. This allows the retrographic sensor to be used advantageously with multiple optical techniques for capturing 3D geometry, including photometric stereo, multiview stereopsis, laser rangefinding, depth from defocus, confocal imaging, and structured light. Photometric stereo is particularly useful for resolving high resolution detail because even small details can yield strong signals when the illumination is at a grazing angle.

One aspect of this disclosure is directed to a system for high-resolution surface visualization. The system comprises the retrographic sensor of this disclosure and a source of illumination or a light path. The system also can include an imaging device. However, an imaging device is not necessary and the image can be visualized by a human eye. In systems for high-resolution visualization, the retrographic sensor is supported on a rigid substrate that is made of glass or another clear rigid material. The source of illumination can include one or more light sources and can illuminate the reflective membrane through the volume of elastomer of the retrographic sensor. The source of illumination can illuminate the reflective membrane at a grazing angle. Alternatively, the system may have in place of, or in addition to, the source of illumination, a light path configured to allow ambient light or light from an external source to illuminate the reflective membrane of the retrographic sensor. The light path can be configured to allow illumination of the reflective membrane at a grazing angle.

When a specimen is brought into contact with the reflective membrane of the retrographic sensor, the reflective membrane conforms to the specimen and takes on the shape of the surface of the specimen. For a completely opaque membrane, light rays that reflect from the particles in the membrane will not be altered by the optical properties of the surface. This property allows for the visualization of surface topography of the specimen independent of the optical properties of the surface.

Another aspect of this disclosure is a system for high-resolution surface measurement. By combining the retrographic sensor with appropriate choices of illumination and 3D measurement algorithms, this system can go beyond visualization and provide accurate high-resolution surface topography measurements. The high-resolution surface measurement system comprises the retrographic sensor, a source of, or path for, illumination, an imaging device, and a processing component.

The retrographic sensor is supported on a clear rigid substrate made of glass or other clear rigid material. The source of illumination can include one or more light sources and can illuminate the reflective membrane through the volume of elastomer of the retrographic sensor. The source of illumination can illuminate the reflective membrane at a grazing angle. Alternatively, the system may have in place of, or in addition to, the source of illumination, a light path configured to allow ambient light or light from an external source to illuminate the reflective membrane of the retrographic sensor. The light path can be configured to allow illumination of the reflective membrane at a grazing angle. The imaging device is positioned to receive light reflected from the reflective membrane in the form of an image and outputting image information. The processing component is coupled to the imaging device and configured to calculate and output measurement information based on image information received from the imaging device.

In some embodiments, the processing component is capable of calculating measurement information using photometric stereo techniques. In some embodiments, the processing component is capable of calculating measurement information using techniques for capturing 3D geometry including, but not limited to, photometric stereo, multiview stereopsis, laser rangefinding, depth from defocus, confocal imaging, and structured light. In some embodiments, the processing component is capable of calculating measurement information using algorithms described herein. In some embodiments, the processing component comprises a processor. As shown in FIG. 1, the processing component can be a computer. FIG. 1 shows a handheld portable measurement system connected to a laptop computer. The computer runs software capable of calculating measurement information. The fingerprint of a finger pressed against the reflective membrane of the retrographic sensor is seen on screen of the laptop.

Illumination

Figure 2A:
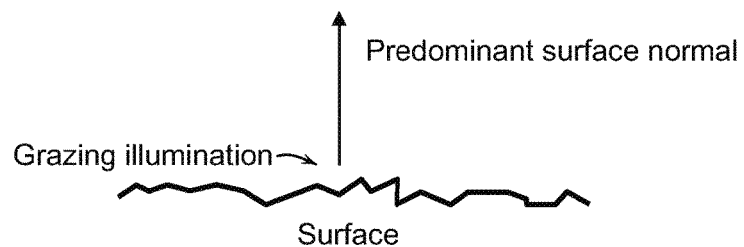
FIGS. 2A-D illustrates several methods for achieving grazing illumination.
Figure 2B:
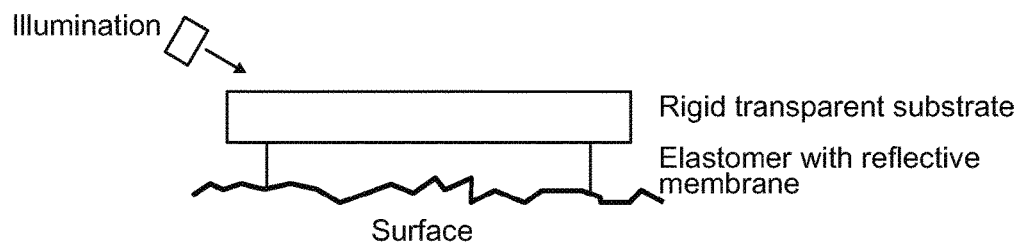
Figure 2C:
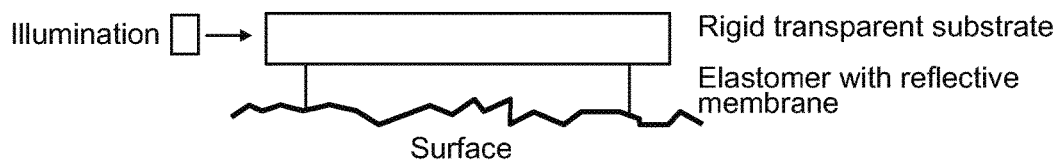
Figure 2D:
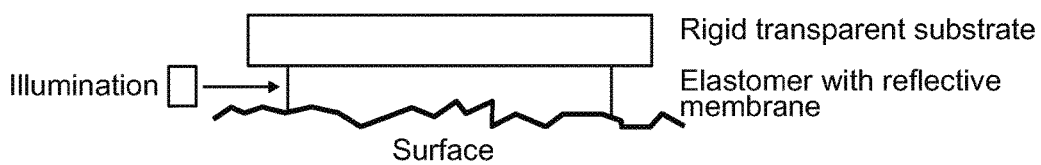

With a matte surface, it is useful to light the surface at a grazing angle, so that the shading signal will be strong. A grazing angle is achieved when the angle between the predominant surface normal and a beam of light incident on the surface is 60 degrees or greater. In other embodiments, this angle is 70 degrees or greater. In other embodiments, this angle is 80 degrees or greater. As seen in FIGS. 2A-D, there are several ways to achieve grazing illumination. FIG. 2A shows bringing light directly to the surface of the specimen at a grazing angle. FIG. 2B shows bringing the light in directly through the rigid substrate at the face of the substrate that is opposite the reflective membrane. FIG. 2C shows bringing the light in through the edge of the rigid substrate, so that it is piped by total internal reflection. FIG. 2D shows bringing the light in through the edge of the elastomer itself. This allows for a lower incident angle because the beam of light is closer to parallel to the reflective membrane.

In some embodiments, the light passes through the air before entering the rigid substrate or the elastomer, resulting in refraction at the air interface. However, in other embodiments, the light originates within a high refractive index medium and does not pass through air. For instance, an LED can be embedded in or optically coupled to the rigid substrate or the elastomer. Alternately, a UV light source can illuminate a fluorescent material that is within or optically coupled to the substrate or the elastomer.

Figure 3A:
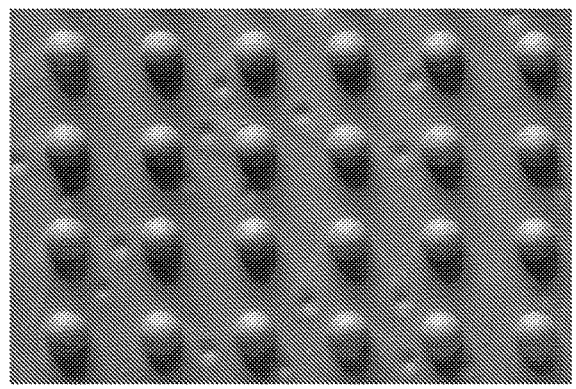
FIGS. 3A-C illustrates how increasing the size of the light source through multiple LEDs can reduce speckle in the image.
Figure 3B:
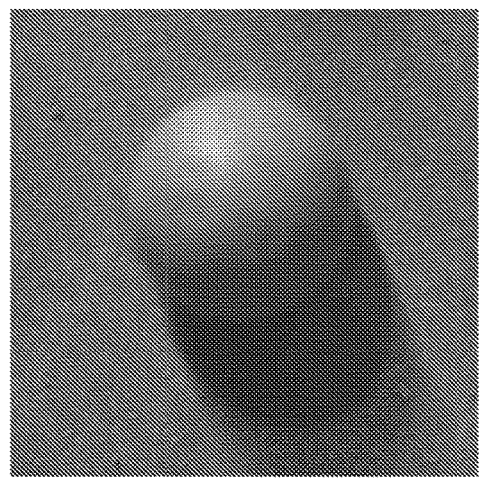
Figure 3C:
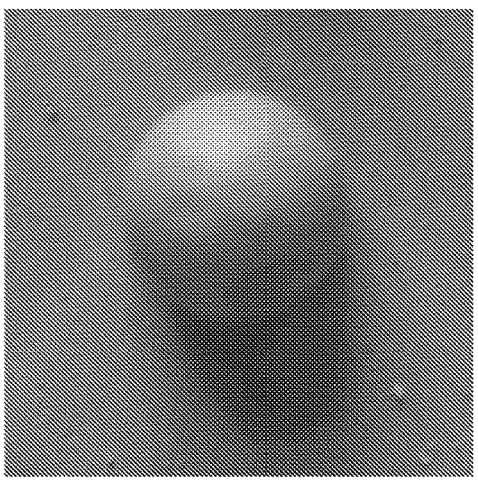

The size of the illumination source influences the presence of speckle in the images. For high-resolution imaging, it is advantageous to have the aperture of the illumination be larger than a single LED. FIGS. 3A-C show how speckle can be reduced by increasing the effective size of the illumination through multiple LEDs. FIG. 3A shows a ball grid array imaged using the retrographic sensor. FIG. 3B shows a single ball contacted with the retrographic sensor illuminated with a single light source. FIG. 3C shows a single ball contacted with the retrographic sensor illuminated with nine LEDs distributed over an area. As can be seen, the color noiselike pattern (speckle) is reduced in FIG. 3C as compared to FIG. 3B.

Figure 4A:
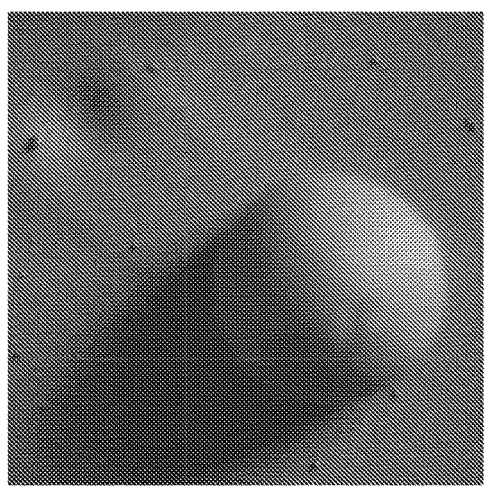
FIGS. 4A-B illustrate how contrast can be increased when using illumination through the side of the clear rigid substrate.
Figure 4B:
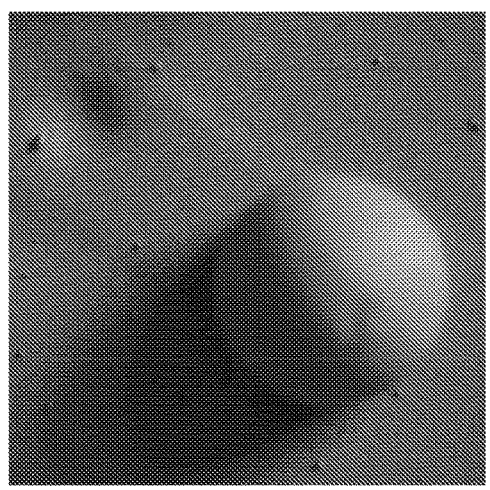

In a design that uses internal reflection within the rigid substrate, contrast can be improved by masking surfaces on the substrate to reduce unwanted reflections. In one embodiment, black paint is applied to the edge of a glass disc everywhere except where small LEDs are optically coupled to the disc. The paint reduces reflections from within the glass disc and improves contrast. The effect can be seen in FIGS. 4A-B. FIG. 4A shows a single ball from a grid array illuminated by a single light source coupled to the side of a glass disc. Light is reflected off the opposite side of the glass disc and illuminated the side of the ball that faces away from the light source. FIG. 4B shows the same setup after painting the edge of the glass disc black. As can be seen, the reflections are reduced and contrast is enhanced in FIG. 4B compared to FIG. 4A.

Visualization and Imaging

When the retrographic sensor is pressed against a surface and illuminated properly, the details of the surface can be seen with the naked eye. This is often sufficient to gain intuition about the surface structure. In some embodiments of the systems and methods described herein, the retrographic sensor is pressed against a surface and viewed directly with a human eye or through magnifying optics. In another embodiment, the retrographic sensor is pressed against a surface and viewed under a microscope. In another embodiment, an imaging device comprising digital camera and appropriate optics to resolve the relevant features of the specimen is used.

Image Processing

Shape-from-shading techniques are particularly useful in combination with the systems of this disclosure for estimating the 3D shape of the specimen in contact with the retrographic sensor. Shape-from-shading refers to a class of techniques that estimate shape from shading information in images, including but not limited to, single-source shape-from-shading, where the image is the result of a single known or unknown illumination condition, and photometric stereo, a technique where two or more distinct illumination conditions illuminate the specimen. For the photometric stereo technique, the illumination conditions typically correspond to illumination from different directions separated in time, resulting in distinct images, or separated in color. U.S. application Ser. No. 12/488,088 described a method using three colored lights coming from different directions, allowing photometric stereo to be conducted with a single image, and therefore enabling real time viewing using a video camera. That method would also be suitable with the systems and methods described herein.

An alternative approach to colored lights is to take several pictures in succession, each with its own illumination. This allows one to use more illumination directions, and may yield more accurate and reliable estimates of surface normal. In principle, a surface normal has two degrees of freedom. A large number of illumination directions will provide additional constraints on the surface normal and allow for robustness to issues such as shadows, albedo changes, and other forms of noise. In some embodiments, four light directions are used. In other embodiments, six light directions are used. In some embodiments where six light directions are used, the lights are arranged in a ring, and each illuminated in sequence. In other embodiments, eight light directions are used. Some considerations for measuring 3D structure using photometric stereo include accurate reflectance modeling, modeling the spatially-varying illumination, and handling shadows.

Although the matte opaque membrane and directional illumination creates a diffuse appearance, it is not perfectly Lambertian. In addition, the illumination is not well-approximated by a point light source due to internal reflections within the glass disc. In order to accurately determine the surface normal from the observed intensity, i.e., the inverse mapping, the forward mapping from surface normal to intensity should be accurately modeled. In one embodiment, a quadratic shading model is used to capture the combined effect of the reflectance function of the reflective membrane and the illumination. The quadratic model is derived from a truncated spherical-harmonic shading model, which has been shown to be a good approximation for Lambertian reflectance under arbitrary illumination conditions. (Basri and Jacobs, *Lambertian Reflectance and Linear Subspaces*, IEEE Transactions on Pattern Analysis and Machine Intelligence (2003) 25:2, pp. 218-233; Ramamoorthi and Hanrahan, *An Efficient Representation For Irradiance Environment Maps*, In Proc. Of SIGGRAPH (2001) pp. 497-500). The quadratic model has nine coefficients which are estimated from the calibration sphere using least squares. This model can fit the appearance of the diffuse (but non-Lambertian) pigment under this particular illumination design.

The grazing illumination achieved by mounting LEDs along the edge of a glass plate is effective at creating contrast, but it no longer fits the assumptions of traditional photometric stereo techniques. In particular, the illumination varies spatially across the image. In order to model the spatially-varying illumination in the system of this disclosure, a dense calibration target was constructed, shown in FIG. 9A. The target consists of an array of spheres (radius 1.5 mm) evenly spaced in a grid. The system automatically calibrates from two color images of the target (6 lighting conditions stored as color channels). The automatic calibration process takes advantage of the even spacing of the spheres and the sharp boundary caused by the grazing illumination to accurately locate the spheres in the image.

The relative positions of the lights varies across the image, as shown by the different shadows cast by each sphere on the calibration target (FIG. 9A). A linear model with three coefficients is fit independently to each sphere. The spatial variation of these coefficients is modeled with a quadratic surface (FIG. 9C).

The coefficients of the illumination model vary smoothly over the image. To model the spatial variation in the coefficients, a quadratic surface using the center of each sphere as the spatial position of the coefficient was used. In FIG. 9C, the measured coefficients are shown for the linear model at each sphere and the quadratic surface.

Due to the grazing illumination, shadows are possible if the object has large depth discontinuities. Most photometric stereo algorithms assume distant illumination and do not model cast shadows. In the presence of cast shadows, however, the estimate of a surface normal will be biased. To reduce the influence of shadows, a weighted least-squares scheme that reduces the constraints from pixels that are in shadow was used.

Once surface normals are estimated at every pixel in the image, depth is reconstructed by integrating the normals. This process is common to many shape-from-X and gradient-domain methods, and is often referred to as "Poisson" integration in the literature. An iteratively reweighted least-squares (IRLS) approach is effective at reducing the influence of noisy surface normal estimates on the resulting surface. In some embodiments, the IRLS procedure is stopped before ten iterations. In other embodiments, the IRLS procedure is stopped after ten iterations.

Accuracy Validation

Figure 10A:
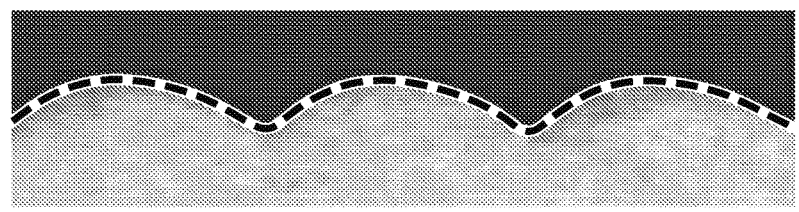
FIGS. 10A-10D show aspects of an accuracy validation against a lenticular microlens array.

The accuracy of the systems and methods was validated by capturing the geometry of a lenticular sheet, a type of microlens array constructed from parallel cylindrical sections. The profile of the sheet is made up of periodic arcs (FIG. 10A). To measure the ground-truth profile, a thin slice was cut from the sheet and photographed it on its side at a spatial resolution of approximately 2 microns per pixel. The image of three arcs from the profile, after thresholding, is shown in FIG. 10A. Points were extracted along the boundary of the arcs and fit a cubic spline to the extracted points using least-squares. The best-fit spline is shown as a dashed line superimposed on the image.

Figure 10B:
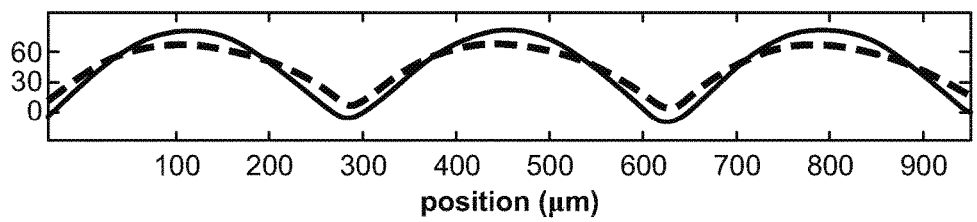
Figure 10C:
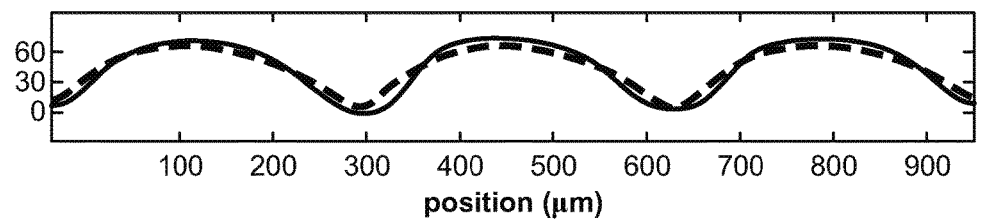
Figure 10D:
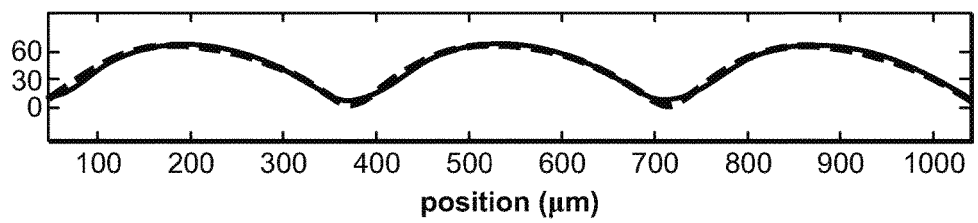

Images were captured from five different sensor positions and the median was computed across the images. FIG. 10A shows the height profile measured from an image of a lenticular array on its side. FIG. 10B shows the reconstructed depth profile (blue, solid) compared to measured profile (red, dashed) using the linear approach, Eqn. 4; the RMS error is 12.4 microns. FIG. 10C shows the reconstructed depth profile using a lookup table approach, similar to the method in (Johnson and Adelson 2009); the RMS error is 8.1 microns. FIG. 10D shows the reconstructed depth profile using this method; the RMS error is 3.0 microns.

Additional Methods for Improving Performance of the High-Resolution Sensor

Methods for Reducing Trapped Air

Entrapped air, i.e., small bubbles that are trapped between the reflective membrane and the surface of the specimen being studied, especially in pits and crevices, causes problems for high-resolution measurements. This disclosure provides several ways of dealing with entrapped air.

In some embodiments, in order to reduce or eliminate trapped air, the reflective membrane is made with a very fine texture that provides minute passages for the entrapped air to escape. This sometimes happens naturally when the reflective membrane is made as a thin layer of particles without a medium or binder. Alternatively, a fine powder (such as talc) can be applied to the reflective membrane or the specimen for the purpose of providing air passages. However, the powder should be sufficiently fine to avoid adding add noise to the measured topography.

If the reflective membrane surface is tacky and smooth, it may trap air bubbles. To avoid this entrapped air, the specimen and/or the reflective membrane may be flooded with a liquid before pressing the reflective membrane against the specimen. Rather than trapping little pockets of air, the reflective membrane will trap little pockets of the liquid. The sensor is then pressed against the specimen for a period of time, typically ranging between 10 and 100 seconds, until the reflective membrane is in continuous contact with the specimen and the liquid has effectively disappeared by either being absorbed into the specimen, being absorbed into the sensor, or being squeezed out to the edges of the sensor. After this period of sustained pressure, the pressure can be released. The tacky reflective membrane then remains in contact with the specimen, even without pressure being applied.

Figure 5A:
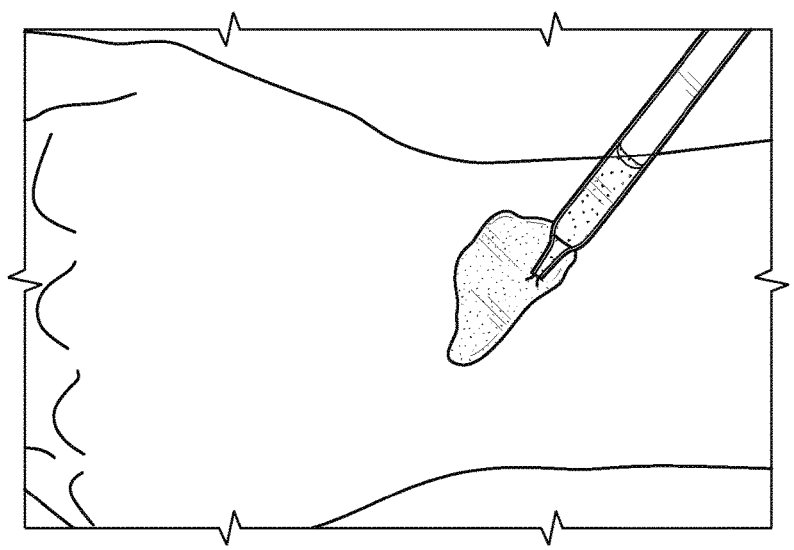
FIGS. 5A-B illustrate the use of a fluid to reduce trapped air when imaging human skin.
Figure 5B:
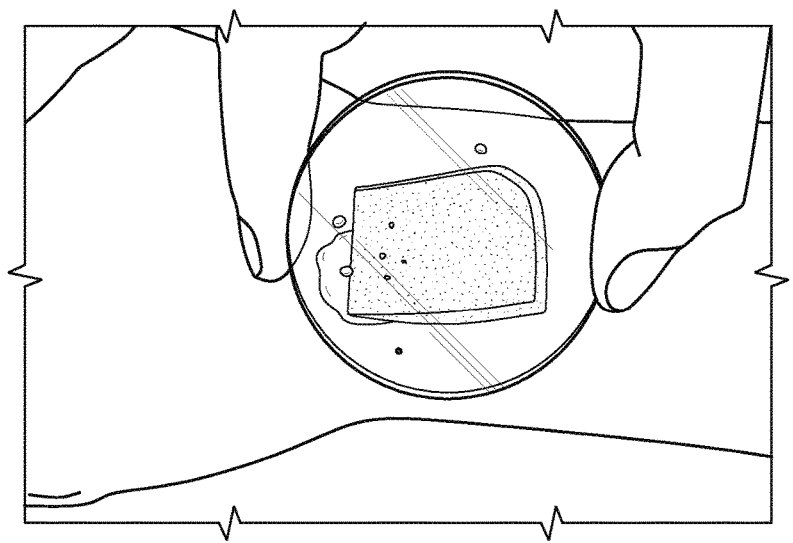

This technique for eliminating air bubbles can be used when using the retrographic sensor on human skin, as shown in FIGS. 5A&B. FIG. 5A shows the skin being wetted before being contacted with the retrographic sensor. FIG. 5B shows the retrographic sensor being pressed against the human skin specimen. After a period of time, all of, or at least a portion of, the liquid will be absorbed or displaced, allowing the specimen and the reflective membrane to come into intimate contact without entrapped air bubbles, thereby allowing improved imaging of the skin.

Liquids used for wetting the specimen or the reflective membrane should be of low viscosity. Examples of liquids that can be used include, but are not limited to, hexamethyldisiloxane, Dow Corning OS-20, isopropyl myristate, and isododecane.

Median Noise Reduction

There are some unwanted effects in the measurement process that can be treated as noise. In particular, there are sometimes random imperfections in the reflective membrane, as well as dust or other debris that may become attached to the membrane. If multiple images are captured with the sensor in different positions (but with the object fixed with respect to the camera), the position of the debris and imperfections will be randomized. By taking the median across multiple scans, the influence of large outliers is avoided. The median approach is only appropriate if the object being measured is rigid.

Computing the median across multiple images requires image alignment. Although the capture setup is rigid, the act of pressing the sensor into the sample can cause shifts in the image of several pixels. A simple image alignment algorithm that is reasonably efficient for this task, even on large images (15 to 18 megapixels), was implemented. The algorithm performs a hierarchical coarse-to-fine grid search over a predetermined range of spatial translations. As an error criterion, the sum of absolute differences, after correcting for multiplicative exposure shifts, was used. To improve efficiency, the computation was performed on a fixed number of windows and the estimates were pooled. These techniques are fairly common for image alignment, and a good overview can be found in a survey by Szeliski, *Image Alignment and Stitching: A Tutorial*, Foundations and Trends in Computer Graphics and Vision (2006), 2:1. Image alignment is also necessary for the raw images from the portable device to reduce the influence of camera shake during the capture sequence.

Methods of Manufacture

A reflective membrane can be made by making a pigment or using commercially available pigments. Examples of commercially available pigments include, but are not limited to, Stone Gray pigment from Mixol, and the like. For example, in the case of a TPE gel, a paint may be made by dissolving the TPE in a solvent such as toluene or xylene, adding the pigment, and then applying the paint to the elastomer surface by spraying or other means. If the membrane needs to be both thin and opaque for the desired imaging application, it should have a high pigment load.

In some embodiments, a thin layer of reflective particles is applied directly to the surface of a sticky or tacky elastomer. The particles adhere to the surface in an approximate monolayer. Because there is no binder (as there is with paint), the particles will not adhere to a tacky elastomer when they are not in contact with the tacky elastomer, thus helping to limit the layer of particles to a monolayer. For example, the adhesive on 3M VHB tape is sufficiently sticky to create a thin and opaque membrane using this method. Gels that are very soft and tacky include the HSSG series of TPE's available from Crinnis Consulting, the soft polyurethanes from Northstar, or the Sylgard 527 silicone from Dow Corning. By carefully dusting the pigment onto the elastomer, it is possible to get a thin, uniform coating. The goal of the dusting technique is to distribute the particles over the surface of the tacky elastomer without scratching or otherwise deforming the surface of the elastomer. Examples of particles that can be dusted onto an elastomer include, but are not limited to, non-specular metal powder, fine aluminum powder, silver microspheres (available from Inframat Advanced Materials), and the like. In such embodiments, this layer of reflective particles on the elastomer is the reflective membrane.

Rather than dusting the particles across a tacky surface, the particles may be suspended in a volatile liquid. Once the particles are suspended in the liquid, the liquid can be applied to the tacky surface by spraying, dipping, dabbing, or other means. Only a very thin layer of particles adheres to the tacky surface, thereby permitting high-resolution imaging.

Figure 6:
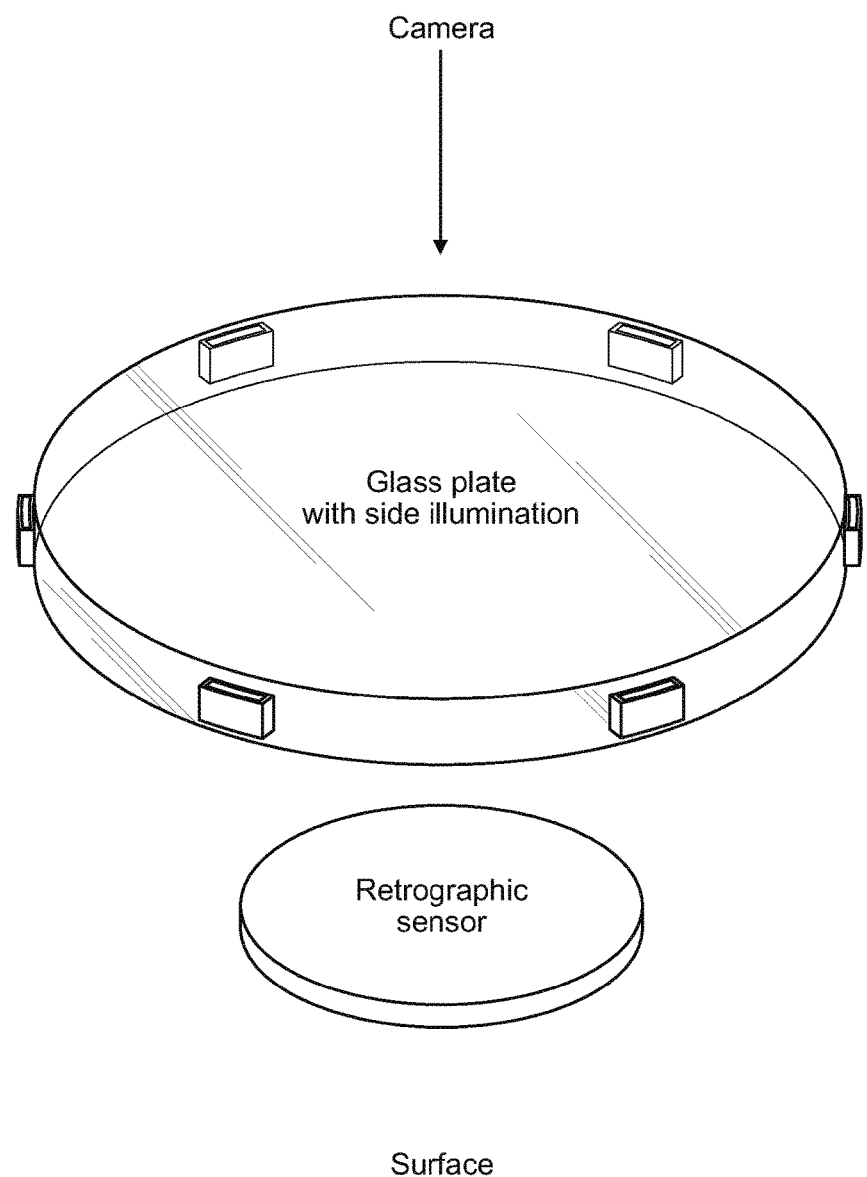
FIG. 6 shows an exemplary configuration of a high-resolution surface visualization or measurement system in an exploded view format.

An Example Configuration for High-Resolution Surface Visualization and Measurement and Two Implementations There are many combinations of elastomer, reflective membranes, illumination, imaging devices, and processing components that can be used for surface visualization and measurement. The choice of each component is influenced by the properties and scale of the features on the object being measured. One example configuration has been shown to be successful for high-resolution surface visualization and measurement. This configuration uses a matte, dark gray retrographic sensor, mounted on a flat, rigid and transparent substrate (e.g., a glass disc), with illumination through the side of the rigid substrate. FIG. 6 shows this configuration in an exploded view format. A camera, or the human eye, views the deviations of the reflective membrane on the retrographic sensor caused by the surface of interest through the rigid substrate. This configuration provides grazing illumination and allows for multiple illumination directions, which may be important for 3D measurement using photometric stereo.

This configuration has been implemented in two ways: a bench system and a portable handheld system. Both the bench and portable implementations use off-the-shelf cameras and optics. In general, the bench configuration allows for higher resolution imaging, or imaging over a larger field of view, due to the broad selection of optics and high pixel count cameras. The off-the-shelf choices for optics and sensors are more constrained for the portable device, so it has a lower pixel count and more compact optics. However, the portable implementation can be used outside the lab, which allows for measurements on the surface of objects too big to bring into the lab (e.g., the wing of an airplane) as well as measuring living samples in place (e.g., plants).

Bench Configuration.

Figure 7:
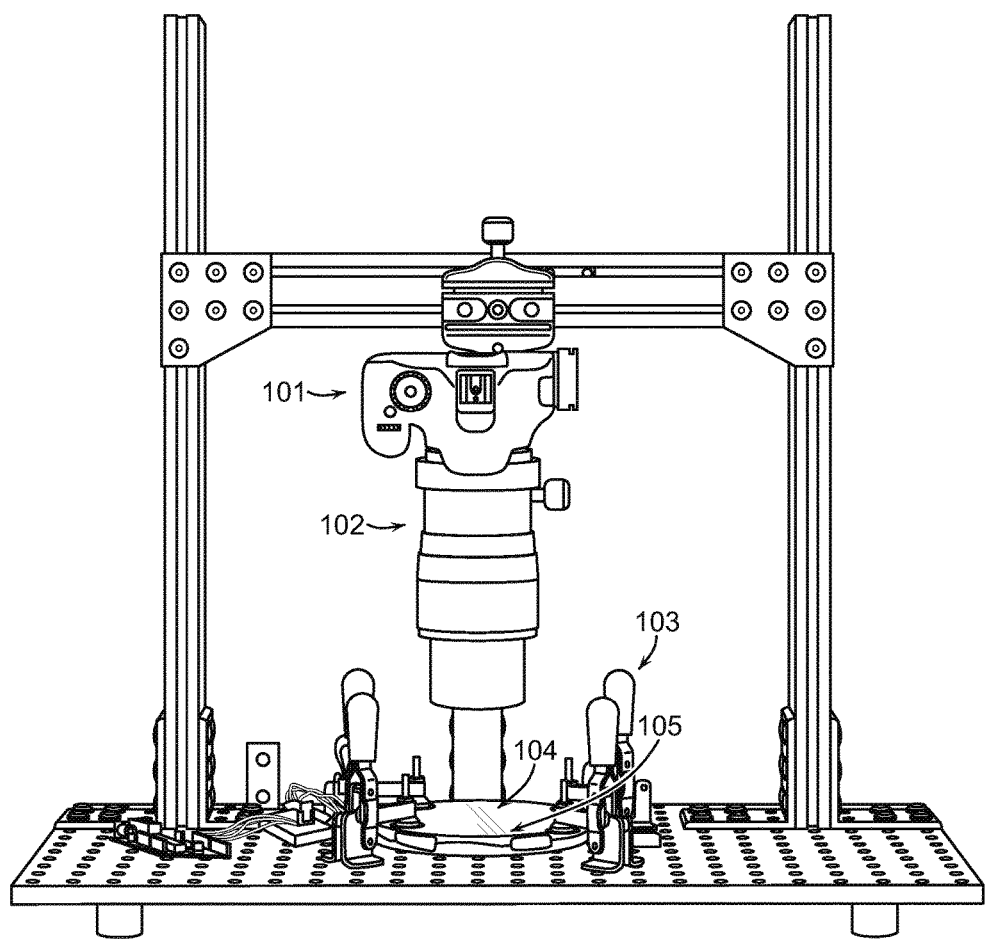
FIG. 7 is an example of a bench configuration of the high-resolution image and measurement system.

An example of a bench configuration (FIG. 7) consists of a 18-megapixel Canon EOS Rebel T2i camera 101 with a Canon MP-E 65 mm macro lens 102 mounted vertically over an optical bench. The elastomeric sensor is mounted on a 0.5-inch thick, 5.5-inch diameter glass plate 104 with six LEDs 105 evenly spaced around the perimeter. The glass plate and sensor are secured to the subject material with toggle clamps 103.

Portable Configuration.

Figure 8:
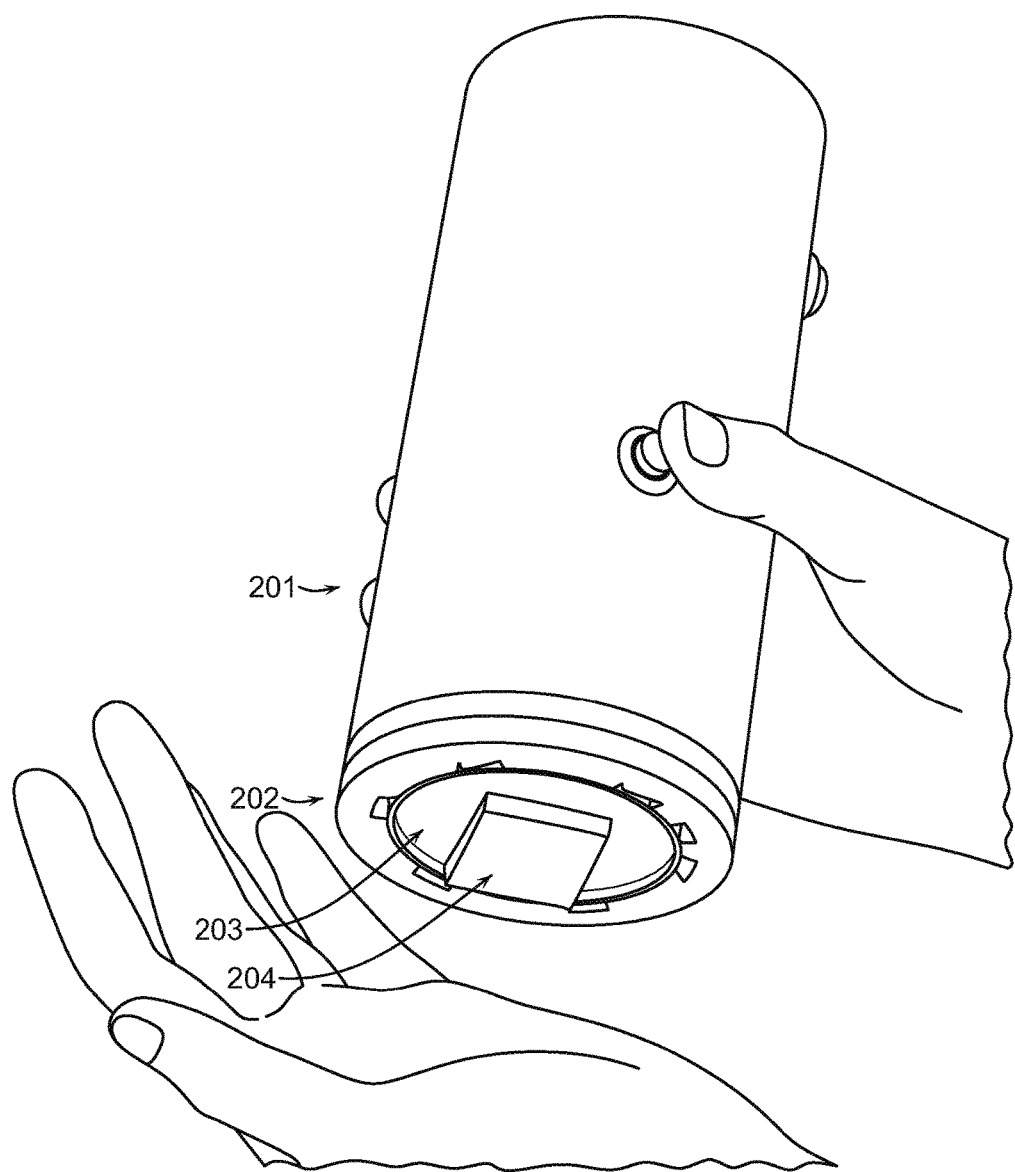
FIG. 8 is an example of a handheld portable configuration of the high-resolution image and measurement system.

An example of a portable configuration (FIG. 8) is constructed from an acrylic tube 201 with a 3-inch outside diameter. Tube 201 is approximately 8 inches long. The sensor 204 is mounted on the exterior of a 0.25-inch thick, 2.25-inch diameter glass plate 203 at one end of the tube. LED 202 leaves the interior of the tube free for a 0.8-megapixel Point Gray Flea2 firewire camera (1032×776 pixels). When the exterior red button is pressed, the system rapidly captures the six lighting conditions.

An Example Configuration for High-Resolution Skin Visualization and Measurement

Measuring the topography of human skin is difficult for several reasons. When placing the elastomer against the human skin, it is normally necessary to apply pressure. This pressure also flattens the skin, which distorts the topography. To avoid this problem, a soft gel elastomer with a tacky surface can be used. For skin measurements, the retrographic sensor is pressed against the human skin and allowed to adhere. Then, the pressure is released. The sensor continues to adhere to the human skin, which can now return to its normal topography, since the very soft sensor is exerting only small forces on it. After the sensor has adhered to the human skin, surface measurements can be taken as described above.

Once the elastomer is in place, it is possible to illuminate it and view it by eye or with a camera. The human skin has, in effect, been painted with a very thin opaque layer that has known optical properties, such as being matte and gray. At this point it becomes possible to measure the skin using any number of techniques. Indeed, there are optical profilometers and 3D scanners known in the art that may be used with matte surfaces that may work well in conjunction with the systems of this disclosure.

Computer vision algorithms (e.g., photometric stereo) can be used to estimate the shape of the surface that contacted the membrane.

EXAMPLES

Example 1

High-Resolution Measurement with Silver Particles

Figure 12A:
FIGS. 12A and 12B show an image and a high-resolution height map of laser-printed text that was measure using silver microspheres dusted onto VHB tape.
Figure 12B:
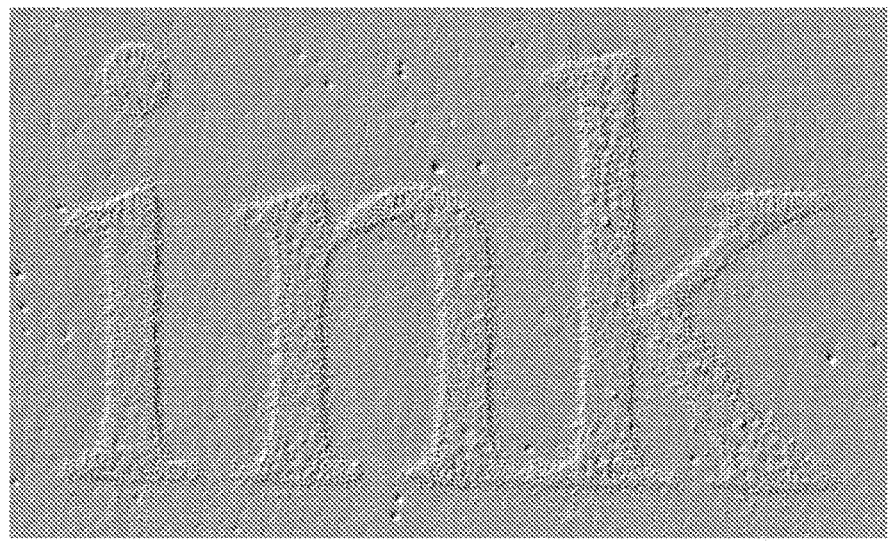

FIGS. 12A&B show a high-resolution height map that was measured using a retrographic sensor comprising silver microspheres dusted onto VHB tape. The 3D information was derived from photometric stereo using edge lit illumination (based on a set of LED's arranged along the edge of the rigid substrate). FIG. 12A is a close-up detail of the word "ink" which has been printed on clay-coated paper with a xerographic printer. FIG. 12B is a rendered height map derived from the same specimen. The individual toner particles, which are 10-20 microns, can be clearly seen.

Figure 13A:
FIGS. 13A and 13B illustrate the effect of pigment size and shape on the quality and resolution of the images captured by the system.

Sensors in U.S. application Ser. No. 12/488,088 used a reflective membrane constructed with a metal-flake pigment. Metal flakes are shiny and the reflected intensity changes rapidly for even small deflections in the surface normal, making shallow surface relief easily visible. However, metal-flake pigment has two important drawbacks. First, when viewed at high-resolution, the flakes themselves are visible and introduce noise, as shown in FIG. 13A. Second, the narrow reflection lobe of the shiny pigment limits the range of surface angles for which a usefully bright image can be recovered (FIG. 14(*a*)). FIG. 14(*a*) shows that a metallic pigment provides good contrast for many lighting conditions, but loses intensity at the steep sides of the sphere.

Figure 13B:
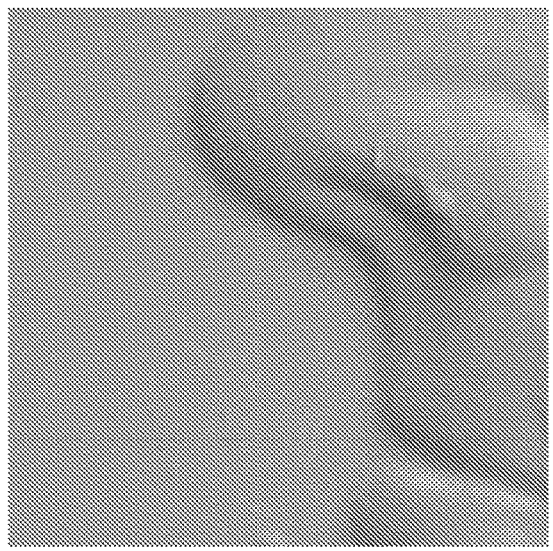

To allow for high-fidelity capture at microscopic scales, the reflective membrane is instead constructed from pigment containing near-spherical particles of silver less than 1 micron across (47MR-21S, Inframat Advanced Materials (www.advancedmaterials.us)). This extremely fine powder appears as a smooth coating even at high-resolution, as shown in FIG. 13B. Both FIGS. 13A & 13B show Roosevelt's nose on a US dime. FIG. 13A shows that, when using metal-flake pigment, the size of the flakes and their random orientations are visible in the image. These effects will cause noise in the estimated surface. FIG. 13B shows that, with silver powder, the average particle size is below 1 micron. The near-spherical shape reduces noise due to random particle orientation.

FIG. 14(*b*) shows that a diffuse pigment under the same illumination as FIG. 14(*a*) has limited contrast. FIG. 14(*c*) shows that grazing illumination improves contrast across the sphere. Luminance histograms are shown below each calibration sphere. Grazing illumination is achieved by placing surface mount LEDs along the edge of a glass plate, as shown on the exploded view diagram (FIG. 14(*d*)).

A metallic pigment is chosen because it is opaque even in a thin layer. The thickness of the membrane affects the ability of the sensor to resolve fine surface detail. A thick membrane acts as a mechanical low-pass filter, attenuating fine detail. For a high-resolution sensor, the membrane should be at most a few microns thick. Pigments that refract light, such as titanium dioxide are not sufficiently opaque in such thin layers. Metallic pigments, however, are reasonably opaque even in thin layers. The silver pigment may be applied without a binder to further limit thickness.

When illuminated, the powder appears diffuse and rather dark. Counterintuitively, a dark sensor is desirable as it reduces inter-reflection between surface features. The diffuse surface reflects illumination at the full range of surface orientations, but can present problems for capture if the illumination is not designed to create sufficient contract. FIG. 14(*b*) shows a calibration sphere pressed into the silver powder membrane with illumination similar to the retrographic sensor of U.S. application Ser. No. 12/488,088; the corresponding intensity histogram is below. The lack of contrast reduces the discriminability of surface orientations and increases the sensitivity to noise.

For a diffuse surface, contrast is maximized under grazing illumination. To create grazing illumination across the sensor, six surface-mounted LEDs are spaced equally around the edge of a glass disc. The glass disc is used as a mounting plate for the elastomeric sensor and the light from the LED's propagates within the disc by total internal reflection. Each LED provides a different lighting condition for photometric stereo. This illumination design dramatically increases contrast, as shown in FIG. 14(*c*).

The resolution of the sensor is also dependent on the rigidity of the elastomer. 3M VHB is used as mounting tape for high-resolution results for hard surfaces. For skin and other soft surfaces, a thick slab of very soft gel elastomer is used to avoid applying too much pressure. Thermoplastic elastomers like those in the Versaflex series from GLS Corp., which can be made even softer by the addition of plasticizer oil, can be used.

Example 2

Comparison with Previous Approach

To demonstrate improvements over the retrographic sensor of U.S. application Ser. No. 12/488,088, improvements in both the resolution and accuracy of the system are shown, especially in regions containing shadows. For a side-by-side comparison of resolution, a high-resolution scan of the $20 bill that was captured with the retrographic sensor of U.S. application Ser. No. 12/488,088 was acquired. A region of a $20 bill shown in FIG. 15A was also scanned with the system of the present disclosure. In FIGS. 15(A-E) both results are shown. FIGS. 15(B) and (D) show a rendering of the high-resolution $20 bill example from the previous retrographic sensor with a close-up view. FIGS. 15(C) and (E) show a rendering of the captured geometry using the new high resolution system of this disclosure. As can be seen, the system of the present disclosure can resolve the individual fibers in the bill.

Figure 11A:
FIGS. 11A and 11B show shadow handling via iteratively reweighted least squares.
Figure 11B:

The importance of handling shadows is also demonstrated in photometric stereo. An ancient Greek coin from the city-state of Taranto was scanned using the system of this disclosure. This coin has significant depth variation that create shadows in the input data (FIG. 11). At the end of the optimization, the weights for each image primarily correspond to shadow regions in the image. The lookup table approach does not account for shadows and artifacts are visible in the reconstructed surface (FIG. 16A). As can be seen, the high-resolution system minimizes the effect of shadows on the reconstruction (FIG. 16B).

Example 3

High-Resolution Measurement with a Tacky Elastomer

Figure 17A:
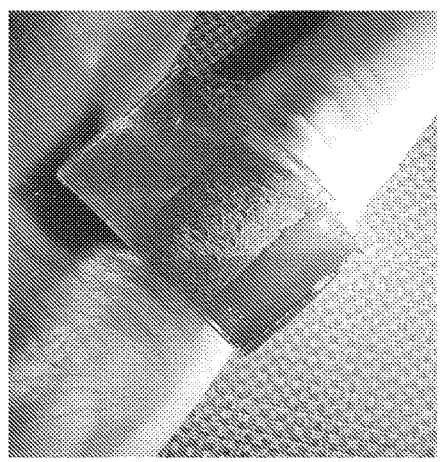
FIGS. 17A-17B show the wrinkles of the skin of a human finger captured through a high-resolution system of this disclosure.
Figure 17B:
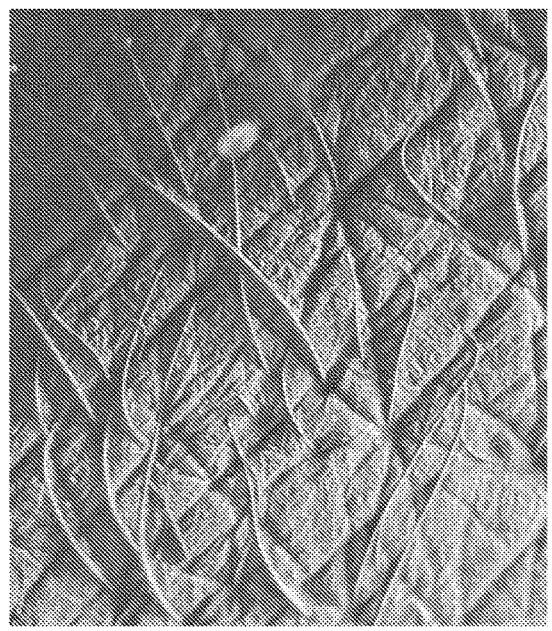

A clear gel elastomer is made of a very soft TPE (HSSG-20) from Crinnis Consulting. The reflective membrane was made by dissolving a soft tacky TPE, also from Crinnis, in toluene and xylene. This was mixed with pigment extracted from Mixol Stone Gray tint, and the mixture was sprayed onto the gel surface with an airbrush. After the reflective membrane was dry, a few drops of hexamethyldisiloxane were placed on the skin of a human finger. The elastomer was mounted on a piece of glass, and then pressed against the finger for 60 seconds. As can be seen in FIG. 17, the procedure successfully solves several problems. FIG. 17A shows a finger in contact with the elastomer. FIG. 17B shows a close-up view of the elastomer in contact with the finger. The skin's wrinkles can be seen, since they are not being squashed from pressure. The reflective membrane is soft enough that it can be considered viscoelastic, and it conforms so well that the hairs are captured. There are no trapped air bubbles. The reflective membrane clings to the finger, remaining in contact without applied pressure by virtue of its tackiness.

Example 4

Capture Examples

Figure 18:
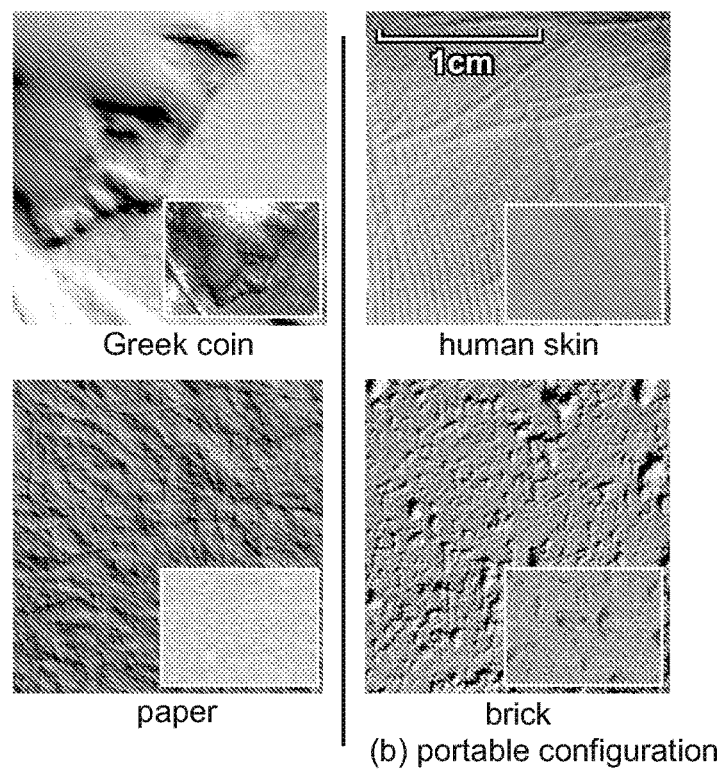
FIG. 18 depicts example geometry measured with the bench (12(a)) and portable (12(b)) configurations.
Figure 18:
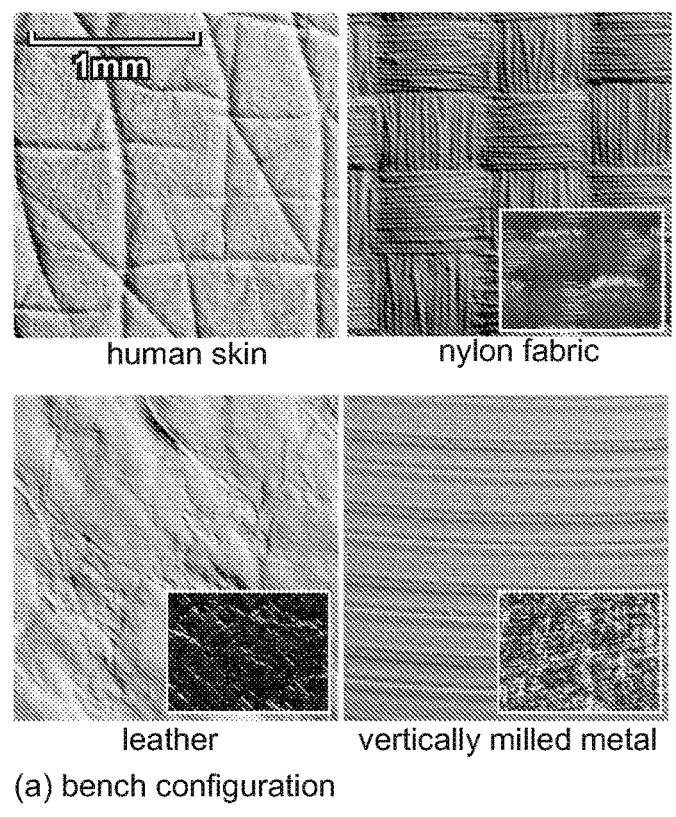

To demonstrate the practicality of the system, the surface structure of a range of common materials was captured, as shown in FIG. 18. Each patch was reconstructed from a set of photographs, captured using the bench configuration. The number of photographs captured depended on the material sample. For rigid materials, 5 images were captured and a median across the images was computed to reduce noise. For materials with delicate structure, such as the fabrics, a single impression was used since the structure would be disturbed across scans. The outer image shows a rendering under direct lighting. The inset image shows the macro photograph of original sample. The scale is shown in upper left.

FIG. 18(a) shows the results from the bench configuration along. The samples include difficult materials like shiny metal and fabric. In many cases, the shape of the sample is hardly recognizable from the photograph (e.g., vertically milled metal, nylon fabric) illustrating the difficulty of capturing the surface with the retrographic sensor of U.S. application Ser. No. 12/488,088.

To demonstrate the portable device, the surface geometry of human skin and brick (captured outside) were captured. These results are shown in FIG. 18(b). The portable device enables texture capture in the field.

Figure 19A:
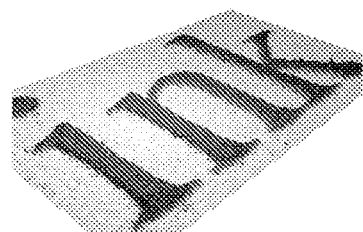
FIGS. 19A-19B show geometry rendered with a color texture map.
Figure 19B:

As a demonstration of scale, a paragraph of text was printed on clay-coated paper and the system literally captured the ink on the page. FIG. 19A shows the rendered geometry with the height scaled by a factor of 10. A color image of the page was used as a texture map. Note that the accumulation of toner particles is visible. FIG. 19B shows the measured geometry of a Greek coin textured with a color photograph.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A high-resolution retrographic sensor, comprising:
   (a) a volume of elastomer capable of transmitting an image;
   (b) a thin, opaque reflective membrane capable of reflecting light covering at least one side of the elastomer, wherein the reflective membrane is arranged to conform to a specimen that contacts the membrane.

2. The retrographic sensor of claim 1, wherein the elastomer comprises silicone rubber, polyurethane, thermoplastic elastomer, plastisol, natural rubber, polyisoprene, polyvinyl chloride, gelatin, hydrogel, or a mixture thereof.

3. The retrographic sensor of claim 1, wherein the reflective membrane is matte.

4. The retrographic sensor of claim 1, wherein the reflective membrane has an opacity of at least 99%.

5. The retrographic sensor of claim 1, wherein the reflective membrane is gray.

6. The retrographic sensor of claim 1, wherein the reflective membrane comprises reflective particles with a mean diameter of less than about 2 microns.

7. The retrographic sensor of claim 1, wherein the reflective membrane comprises reflective particles in a monolayer.

8. The retrographic sensor of claim 1, wherein the reflective membrane comprises metal particles.

9. A high-resolution visualization system, comprising:
   (a) a retrographic sensor supported on a clear rigid support, wherein the retrographic sensor comprises:
      (i) a volume of elastomer capable of transmitting an image;
      (ii) a thin, opaque reflective membrane capable of reflecting light covering at least one side of the elastomer,
      wherein the reflective membrane is arranged to conform to a specimen that contacts the membrane; and
   (b) a source of illumination positioned to illuminate the reflective membrane.

10. The system of claim 9, wherein the source of illumination is positioned to illuminate the reflective membrane at a grazing angle.

11. The system of claim 9, wherein the source of illumination comprises one or more light sources.

12. The system of claim 9, further comprising an imaging device positioned to receive light reflected from the reflective membrane in the form of an image.

13. The system of claim 12, wherein the imaging device comprises a camera.

14. The system of claim 9, wherein the system is portable.

15. The system of claim 9, wherein the reflective membrane comprises metal particles.

16. The system of claim 9, wherein the reflective membrane is matte.

17. A high-resolution measurement system, comprising:
   (a) a retrographic sensor supported on a clear rigid support, wherein the retrographic sensor comprises:
      (i) a volume of elastomer capable of transmitting an image;
      (ii) a thin, opaque reflective membrane capable of reflecting light covering at least one side of the elastomer,
      wherein the reflective membrane is arranged to conform to a specimen that contacts the membrane;
   (b) a source of illumination positioned to illuminate the reflective membrane;
   (c) an imaging device positioned to receive light reflected from the reflective membrane in the form of an image and configured to output image information; and
   (d) a processing component coupled to the imaging device and configured to calculate and output measurement information based on the image information received from the imaging device.

18. The system of claim 17, wherein the source of illumination is positioned to illuminate the reflective membrane at a grazing angle.

19. The system of claim 17, wherein the source of illumination comprises one or more light sources.

20. The system of claim 17, wherein the imaging device comprises a camera.

21. The system of claim 17, wherein the processor is configured to calculate the measurement information using a shape from shading technique.

22. The system of claim 17, wherein the system is portable.

23. The system of claim 17, wherein the reflective membrane comprises metal particles.

24. The system of claim 17, wherein the reflective membrane is matte.

* * * * *